United States Patent [19]

Konishi et al.

[11] 4,341,782
[45] Jul. 27, 1982

[54] PYRIMIDINE DERIVATIVES AND AGRICULTURAL USES

[75] Inventors: Kazuo Konishi, Takatsuki; Kazuho Matsuura, Kyoto, both of Japan

[73] Assignee: Takeda Chemical Industries, Ltd., Osaka, Japan

[21] Appl. No.: 147,148

[22] Filed: May 6, 1980

[30] Foreign Application Priority Data

May 15, 1979 [JP] Japan .................................. 54-60069

[51] Int. Cl.³ .................. A61K 31/505; C07D 239/42
[52] U.S. Cl. ..................................... 424/251; 544/253; 544/262; 544/292; 544/330; 544/332
[58] Field of Search ............... 544/262, 292, 253, 330, 544/332; 424/251

[56] References Cited

PUBLICATIONS

Claesen et al., Bull. Soc. Chim. Belg. 68, pp. 47-58, 1959.
Brown, The Pyrimidines Supplement I, pp. 22-23, pub. by Wiley-Interscience (1970).

Primary Examiner—Paul M. Coughlan, Jr.
Attorney, Agent, or Firm—Wenderoth, Lind & Ponack

[57] ABSTRACT

Novel pyrimidine derivatives of the formula;

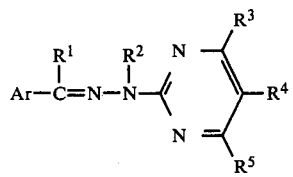

wherein Ar is phenyl or naphthyl, which may be substituted by lower alkyl, lower alkoxy, lower alkylthio, lower alkylsulfinyl, lower alkylsulfonyl, halogen, nitro, trifluoromethyl or di-lower alkylamino; $R^1$ is lower alkyl, lower cycloalkyl, trifluoromethyl, lower alkoxycarbonyl, phenyl or benzyl, and the phenyl may be substituted by halogen; $R^2$ is hydrogen or lower alkyl; $R^3$, $R^4$ and $R^5$ are hydrogen, lower alkyl, lower alkenyl or lower alkoxy, or $R^3$ and $R^4$ or $R^4$ and $R^5$ combine with each other to represent trimethylene, tetramethylene or butadienylene, or salts of them, are excellent antimicrobial agents.

8 Claims, No Drawings

PYRIMIDINE DERIVATIVES AND AGRICULTURAL USES

The present invention relates to novel pyrimidine derivatives, methods for production thereof, and antimicrobial agents for agricultural uses featured by containing one or more kinds of the derivatives as the active ingredient or ingredients. More particularly, the invention relates to a pyrimidine derivative of the formula:

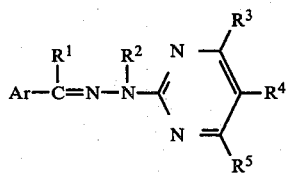
(I)

wherein Ar is phenyl or naphthyl, which may be substituted by lower alkyl, lower alkoxy, lower alkylthio, lower alkylsulfinyl, lower alkylsulfonyl, halogen, nitro, trifluoromethyl or di-lower alkylamino; $R^1$ is lower alkyl, lower cycloalkyl, trifluoromethyl, lower alkoxycarbonyl, phenyl or benzyl, and the phenyl may be substituted by halogen; $R^2$ is hydrogen or lower alkyl; $R^3$, $R^4$ and $R^5$ are hydrogen, lower alkyl, lower alkenyl or lower alkoxy, or $R^3$ and $R^4$ or $R^4$ and $R^5$ combine with each other to represent trimethylene, tetramethylene or butadienylene, or a salt thereof, a method for producing a pyrimidine derivative (I) or a salt thereof which comprises reacting an aromatic ketone of the formula:

ArCOR$^1$    (II)

wherein the symbols in the formula are as defined above, with 2-pyrimidylhydrazine of the formula (III):

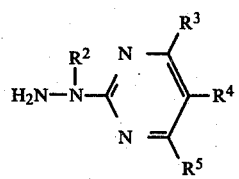
(III)

wherein the symbols in the formula are as defined above, or a salt thereof, a method for producing a pyrimidine derivative of the formula (VI):

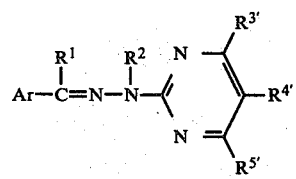
(VI)

wherein the symbols in the formula are as defined below, or a salt thereof which comprises reacting amidinohydrazone of the formula:

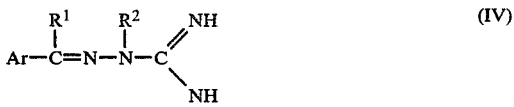
(IV)

wherein the symbols in the formula are as defined above, or a salt thereof, with β-diketone of the formula:

(V)

$R^{3'}$—COCHCO—$R^{5'}$
           |
          $R^{4'}$ wherein $R^{3'}$, $R^{4'}$ and $R^{5'}$ are hydrogen, lower alkyl or lower alkenyl or $R^{4'}$ is lower alkoxy, or $R^{3'}$ and $R^{4'}$ or $R^{4'}$ and $R^{5'}$ combine with each other to represent trimethylene or tetramethylene, and to an antimicrobial agent for agricultural uses which contains as the active ingreadient or ingredients one or more kinds of the pyrimidine derivatives (I) or their salts.

With the increase of food production set as the most urgent goal, large numbers of organometalic bactericides and fungicides, mainly organomercurial preparations, were manufactured in enormous quantities, and had been widely used for long years because of their outstanding effects. The use of such antimicrobial agents, apart from their intended effects produced, brought about simultaneously a variety of undesirable, negative impacts on man and animals and environment, and came to present a social problem. In place of these organometallic compounds, there have emerged, up to now, antibiotics, organic phosphorus compounds, organic chlorine compounds, etc. In spite of the fact that a multiple number of disease injuries usually take place simultaneously in the cultivation of crops, however, the currently prevalent, non-metallic antimicrobial agents, as described hereinbefore, all show a strong selectivity and a narrow antimicrobial spectrum, and many of them are effective merely against a particular, single disease injury. Consequently, use of a mixed preparation by way of a combined utilization of a multiple number of active substances is largely relied upon, inevitably, from a standpoint of the labor-saving, simultaneous pest controlling. This does not necessarily seem desirable in the respects of impact on the environment, efficient use of resources, reduction of expenditures and so on. Furthermore, there still remain some kinds of disease injuries which have not been able to be overcome satisfactorily by these antimicrobial agents alternatively introduced. As the disease affecting the paddy rice culture, for example, there may be mentioned blast of rice plant, sheath blight leaf spot of rice plant, stem-rot of rice plant, Helminthosporium leaf spot of rice plant, bacterial leaf blight of rice plant. As to the first two diseases, there are currently some antimicrobial agents available for individually controlling these to a limited extent, whereas the others have been left unsolved. Especially, the third and fourth diseases have begun to occur conspicuously to the severest degree in recent years, and strongly demanded is the appearance of such an antimicrobial agent as may have the excellent effectiveness against the first two diseases and simultaneously exhibit a similarly excellent controlling effect against the others. The case is basically the same with the disease affecting the dry field farming, fruit culture, floriculture, etc., for example, dawny mildew of cucumber, gray mold of strawberry, stem rot of kidney bean, powdery mildew of barley, gray mold of lettuce, late blight of tomato, leaf blight of cucumber and so on.

The present inventors, as the results of considerable and extensive research work conducted with a specific view to complying with such demands, discovered that a novel pyrimidine derivative of the formula (I) or a salt thereof, being somewhat different in the type of compound from conventional antimicrobial agents and having the hydrazone linkage in the molecule, would possess the nature suited for solving these problems at once, and have, based on the new finding, come to completion of this invention.

Referring to the formulas (I), (II), (IV) and (VI), Ar represents phenyl or naphthyl. In the case of Ar being naphthyl, the position of its bonding may be either in the α- or β-position. Both of these aromatic radicals may be unsubstituted, and the phenyl group may have one to five substituents, while the naphthyl may have one to seven substituents. Examples of such substituents may include lower alkyls, preferably having 1 to 4 carbon atoms, such as methyl, ethyl, n-propyl, i-propyl, n-butyl, i-butyl, sec-butyl and t-butyl; lower alkoxys, preferably having 1 to 4 carbon atoms, such as methoxy, ethoxy, n-propoxy, i-propoxy, n-butoxy, i-butoxy and sec-butoxy; lower alkylthio groups, preferably having 1 to 4 carbon atoms, such as methylthio, ethylthio, n-propylthio, i-propylthio, n-butylthio, i-butylthio, sec-butylthio and t-butylthio; lower alkylsulfinyl groups, preferably having 1 to 4 carbon atoms, such as methylsulfinyl, ethylsulfinyl, n-propylsulfinyl, i-propylsulfinyl, n-butylsulfinyl, i-butylsulfinyl, sec-butylsulfinyl and t-butylsulfinyl; lower alkylsulfonyl, preferably having 1 to 4 carbon atoms, such as methylsulfonyl, ethylsulfonyl, n-propylsulfonyl, i-propylsulfonyl, n-butylsulfonyl, i-butylsulfonyl, sec-butylsulfonyl and t-butylsulfonyl; halogen atoms such as fluorine, chlorine, bromine and iodine; nitro; trifluoromethyl; and di-lower alkylamino groups such as dimethylamino, diethylamino, methylethylamino, methyl-i-propylamino, di-n-propylamino, di-i-propylamino, di-n-butylamino and di-i-butylamino. When not less than two of these substituents occur, they may be not only the same but also different substituents present in not less than two kinds mixed. Among these substituents, lower alkyl, lower alkoxy, lower alkylthio, halogen atom and trifluoromethyl are preferably employed, and lower alkyl such as methyl and ethyl and halogen atoms such as chlorine and bromine are particularly preferred. As to the position of substitution, the phenyl may be substituted by any kind of substitutes in any number at any position, only if the number of substituent is not less than 5, and preferably by the substituent in at least one o-position (2-position), whereby the particularly preferred substituents are lower alkyls such as methyl and ethyl and halogen atoms such as chlorine and bromine. As to the second through fourth substituents, the above-mentioned substituents may, or may not, enter, in any combination, any remaining positions. However, 1 through 4 in the total number of substituents is particularly preferred and, in view of the tendency that even the abovementioned substituents, when they enter both of the o-positions (2,6-positions) at the same time, generally prove difficult to form a hydrazone linkage, not more than 4 in the number of substituents is especially desirable. Analogously, the same thing is true with α- and β-naphthyl groups. For example, it is preferable that a substituent exists at the 2-position in the case of α-naphthyl and at the 1- or 3-position in β-naphthyl, whereby as the preferred substituents are operable the lower alkyls and halogen atoms as mentioned above for the phenyl group. Other substituents may exist at any of the remaining positions, although they preferably enter the 4- or/and 6-positions. It should be noted, however, that the total number of such substituents of 1 or 2 is especially desirable.

$R^1$ in the formulas (I), (II), (IV) and (VI) represents, for example, lower alkyls, preferably having 1 to 4 carbon atoms, such as methyl, ethyl, n-propyl, i-propyl, n-butyl, i-butyl, sec-butyl and t-butyl; lower cycloalkyls such as cyclopropyl and cyclopentyl; trifluoromethyl; lower alkoxycarbonyl groups, preferably having 1 to 4 carbon atoms, such as methoxycarbonyl and ethoxycarbonyl; phenyl and benzyl, and the phenyl may be substituted by a halogen as described above and may, for example, be o-, m- or p-chlorophenyl and the like. Among these substituents, lower alkyl and lower cycloalkyl are preferably employed, and lower alkyl such as methyl and ethyl are particularly preferable.

$R^2$ in the formulas (I), (III), (IV) and (VI) represents hydrogen atom and lower alkyls, preferably having 1 to 4 carbon atoms, such as methyl, ethyl, n-propyl, i-propyl, n-butyl, i-butyl and sec-butyl. Among these substituents, hydrogen atom is especially desirable.

$R^3$, $R^4$ and $R^5$ in the formulas (I) and (III) as well as $R^{3'}$, $R^{4'}$ and $R^{5'}$ in the formulas (V) and (VI) indicate hydrogen atom; lower alkyls, preferably having 1 to 4 carbon atoms, such as methyl, ethyl, n-propyl, i-propyl, n-butyl, i-butyl, sec-butyl and t-butyl; lower alkenyls, preferably having 1 to 4 carbon atoms, such as vinyl, allyl, crotyl and methallyl; and, lower alkoxy groups, preferably having 1 to 4 carbon atoms, such as methoxy, ethoxy, n-propoxy, i-propoxy, n-butoxy, i-butoxy and sec-butoxy. Among these substituents, hydrogen atom, lower alkyl and lower alkenyl are preferably employed, and lower alkyl such as methyl and ethyl and lower alkenyl such as allyl are particularly preferable. Further, at least one of $R^3$, $R^4$ and $R^5$ or $R^{3'}$, $R^{4'}$ and $R^{5'}$ may be lower alkyl as mentioned above to obtain a good result. In other expression, it is particularly preferable that $R^3$ and $R^{3'}$ are lower alkyls such as methyl and ethyl, $R^4$ and $R^{4'}$ being hydrogen or lower alkyls such as methyl and ethyl, and $R^5$ and $R^{5'}$ are lower alkyls such as methyl and ethyl. Where $R^3$, $R^4$ and $R^5$, or $R^{3'}$, $R^{4'}$ and $R^{5'}$ are lower alkyls, they may each be the same as the others or different from one another. Furthermore, $R^3$ and $R^4$ or $R^4$ and $R^5$ combine with each other to represent trimethylene, tetramethylene or butadienylene, while $R^{3'}$ and $R^{4'}$ or $R^{4'}$ and $R^{5'}$ combine with each other to represent trimethylene or tetramethylene. Thus, this means that $R^3$ and $R^4$ or $R^4$ and $R^5$, or $R^{3'}$ and $R^{4'}$ and $R^{5'}$ combine with each other to form a connective,,crosslinking bond and cooperate with two carbon atoms of the pyrimidine ring to form a saturated or unsaturated, 5- or 6-membered condensed carbon ring. When $R^3$ and $R^4$ or $R^4$ and $R^5$ combine with each other to form a butadienylene, this means that they form a benzene ring in conjunction with two carbon atoms of the pyrimidine ring, or, as the whole of the ring, form benzopyrimidine or a quinazoline ring. When $R^3$ and $R^4$ or $R^4$ and $R^5$, or $R^{3'}$ and $R^{4'}$ or $R^{4'}$ and $R^{5'}$ combine with each other to form a tetramethylene group, it means the formation of tetrahydrobenzopyrimidine or a tetrahydroquinazoline ring. Among these substituents, the butadienylene group is especially desirable.

A pyrimidine derivative (I) or a salt thereof is produced, for example, by reacting an aromatic ketone (II) with a 2-pyrimidylhydrazine (II) or a salt thereof.

In conducting the reaction of an aromatic ketone designated by the formula (II) with 2-pyrimidylhydrazine indicated by the formula (III), the latter may be subjected to the reaction, either in the free state or as a salt with an organic or inorganic acid. As the organic acid, employable are formic acid, acetic acid, propionic acid, etc., and as the inorganic acid, employable are hydrochloric acid, sulfuric acid, phosphoric acid, etc. The reaction is carried out by mixing of the two compounds (II) and (III) or a salt thereof in the proportion of about equimolar amounts, although a slightly excessive amount of either of the two may be charged. When the aromatic ketone (II) is liquid, for example, it may be used in excess to allow to act as a solvent as well. Furthermore, when both of the compounds are solid, they may be melted into the liquid state by heating. In order to allow the reaction to proceed smoothly, however, the reaction is preferably carried out in an organic solvent, whereby the organic solvent may be any type of solvents, unless they exert any adverse effect upon the reaction. Particularly preferred are, for example, alcohols such as methanol, ethanol, propanol, butanol, etc. and methyl cellosolve, ethyl cellosolve and the like, ethers such as diethyl ether, tetrahydrofuran, dioxane and dimethoxyethane, aromatic hydrocarbons such as benzene, toluene and xylene, and the like. These solvents may be used, solely or as a mixture of two or more of them at varying mixing ratios.

The reaction, generally, proceeds smoothly. Therefore, heating is not always required, when sufficient stirring or shaking is accompanied, but is sometimes required, if the completion of the reaction within a short period of time is desired. The reaction temperature, normally, is desirably in the range of 30° C. to 150° C., although a higher temperature near to 200° C. is in some instances required. Normally, the reaction is conducted at atmospheric pressure and, in some cases, can be carried out under elevated pressure applied with the use of a tightly sealed container. The reaction time, which varies with the kinds of starting materials and solvents and reaction temperature, goes ordinarily to completion within several ten minutes to some hours, and yet, in some instances extends to several ten hours.

This reaction involves essentially the formation of hydrazones through dehydration condensation reaction of ketones with hydrazines, whereby no particular attention need be paid to moisture removal or dehydration of the reaction system under normal reaction conditions. In cases where acceleration of the reaction rate or enhancement of the yield is desired, however, satisfactory results may in some instances be given by employing both starting materials and solvent adequately dried and dehydrated, and paying attention to prevention of the moisture from entering during reaction, and taking water produced in the reaction system out of the system through azeotropic distillation or adding a dehydrating agent such as molecular sieve to the reaction system.

Although the presence of a catalyst in this reaction is not essential, addition of traces of an acid or base results, in some cases, in marked acceleration of the rate of reaction. Such acid may be either organic or inorganic acid. As the organic acid, employable are formic acid, acetic acid, propionic acid, etc., which may be made to serve as a solvent as well; examples of the inorganic acid which is employable include hydrochloric acid, sulfuric acid, phosphoric acid and polyphosphoric acid (PPA), polyphosphoric acid ester (PPE), titanium tetrachloride, boron trifluoride, and other Lewis acids, etc., whereby sulfuric acid, polyphosphoric acid (PPA), etc., among these, may be made to serve both as a solvent and a dehydrating agent. The bases which are usable include, for example, inorganic bases such as potassium hydroxide, sodium hydroxide and sodium alcoholate, and organic bases such as pyridine and triethylamine, wherein the latter may be made to serve as a solvent. In addition, acidic or basic ion exchange resins may be employed as a solid catalyst. Furthermore, when hydrazine (III) as an acid salt is subjected to reaction as mentioned above, this means that the acid as a catalyst is introduced into the reaction system. Generally speaking, it is the acids which can produce, as the catalyst, the more desirable results in terms of the rate of reaction, yield, coloration, etc.

A pyrimidine derivative (VI) or a salt thereof may also be produced by reacting amidinohydrazone (IV) or a salt thereof with β-diketone (V).

In the reaction of an amidnohydrazone represented by the formula (IV) with a β-diketone designated by the formula (V), the former may be subjected to the reaction, either in the free state or as an acid salt with such an organic or inorganic acid as mentioned hereinbefore. This reaction is conducted by mixing nearly equimolar amounts of both compounds (IV) and (V) or a salt thereof, although either of these may in some cases be charged in slightly excessive amount. In the case of a β-diketone (V) being liquid, for example, it may be employed in excess so as to make it serve as the solvent. Where both are in the solid state, they may be melted and liquefied by heating. Yet, this reaction is generally conducted preferably in an organic solvent so as to allow it to proceed smoothly, whereby such organic solvent may be any type of solvent, unless it affects adversely the reaction; for example, alcohols, ethers, aromatic hydrocarbons, etc. as mentioned above in the reaction of (II) and (III), are particularly preferable. These solvents may be used, solely or as a mixture of two or more kinds thereof at different mixing ratios.

This reaction generally proceeds smoothly. Therefore, heating is not always required, when sufficient stirring or shaking is accompanied, but is sometimes required, if the completion of the reaction within a short period of time is desired. The reaction temperature, normally, is preferably in the range of 40° C. to 200° C., and desirably kept especially within the range of 60° C. to 150° C. Ordinarily, the reaction is conducted at atmospheric pressure and, in some instances, may be carried out under elevated pressure applied with the use of a tightly sealed container. The reaction time, which varies with the kinds of starting materials and solvents and reaction temperature, goes normally to completion within several ten minutes to some hours and, in some cases, extends to several ten hours.

This reaction involves essentially the formation of a pyrimidine ring through the dehydration condensation reaction of an amidine with a β-diketone, and as to the dehydrating conditions and catalyst effects in the reaction system, almost the same things as described in the reaction between (II) and (III) or a salt thereof may be applicable.

The end point of the reaction between (II) and (III) or a salt thereof or between (IV) or a salt thereof and (V) may be easily ascertained by thin layer chromatography, for example. Thus, the reaction may be completed at the time when a spot other than those of starting materials becomes able to be detected on thin-layer silica gel by ultraviolet irradiation (2536 Å) or sprayed Dragendorff reagent.

The pyrimidine derivatives (I) or salts of them produced in this manner are novel compounds which have not been descrived in the literature. The derivatives, normally at room temperature, are colorless or slightly colored, crystalline solid or viscous oil, and present a starch-syrup-like or glass-like semi-solid state, when they are highly viscous. Generally, these are almost insoluble in water but well soluble in various organic solvents, for example, alcohols, ethers and aromatic hydrocarbons being employed in the reaction as well as aliphatic halogenated hydrocarbons such as chloroform and methylene chloride, esters such as ethyl acetate and butyl acetate, acid amides and nitriles such as dimethylformamide and acetonitrile, and the like. Consequently, when the derivative is a crystalline solid, after the completion of the reaction, the reaction mixture is directly cooled, or admixed with water in the case of the reaction solvent being miscible with water, or freed of the reaction solvent, and the resultant crude product is recrystallized from an appropriate solvent. When it is an oily substance, the crude product obtained by the similar treatment is purified by the use of column chromatography. In cases in which an acidic or basic catalyst is added or an acidic or basic solvent is employed, neutralization treatment must be carried out in accordance with the nature of the solution. When an acidic catalyst or an acidic solvent is used, the above-mentioned treatment may directly be carried out to isolate the reaction product as an acid salt. Further, the reaction product, once having been isolated as a free base, may be derived into salts with a variety of organic or inorganic acids as mentioned above in 2-pyrimidylhydrazine (III), if desired, and the resultant acid salts, together with a free base, are contained in the desired compound (I). The structure of a reaction product may be confirmed by elementary analysis, infra-red absorption spectra, ultraviolet absorption spectra, mass spectra, nuclear magnetic resonance spectra, etc.

The pyrimidine derivative (I) or a salt thereof, a reaction product of the above-mentioned reaction, is a kind of hydrazone compound having a C=N double bond in the molecule and, consequently, exist in two geometrical isomers, Z and E types, in connection with this bond. For example, there is often observed the formation of two isomers as two adjacent spots on the thin layer chromatogram obtained with a crude reaction product. Yet, the proportion of two isomers varies depending upon kinds of starting materials and solvents, reaction conditions (temperature and duration time), the acidity of a solution, type of catalysts and with or without addition thereof, etc., and the single isomer alone may be produced, as the case may be. In cases where the isomers are produced as a mixture, they may be isolated by carrying out thoroughly purification by means of column chromatography, for example. In this case, it often occurs that elution with chloroform elutes the Z-isomer faster, while elution with ethyl acetate elutes the E-isomer more quickly. As to the identification of the isomers, each of them may be discriminated by chemical shifts of proton signals in the NH of the molecules in the nuclear magnetic resonance spectra. In other words, the chemical shift for the E-isomer, normally in many cases, is located relatively at the lower magnetic field than that for the Z-isomer. Consequently, the isomer ratio of the mixture may be determined by the integrated intensity ratio for each of the peaks. However, these isomers are tautomeric, being vulnerable to isomerization by heating and light irradiation, and it is therefore useless to isolate forcibly the mixture of isomers to each isomer in case where the isolation is difficult, while there is no adverse effect in subjecting the mixture of isomers to the application fields of the present invention.

Referring now to the starting materials to be used in the above-mentioned reactions, the aromatic ketone represented by the formula (II), as described on the lists of various reagent makers home and abroad, is readily available in many kinds. The others may be easily synthesized by conventional methods of aromatic ketone synthesis, for example, by the general synthesis methods such as Friedel-Crafts acylation reaction of aromatic hydrocarbons with carboxylic acids or their derivatives, and those in accordance with such reaction [G. A. Olah (Editor), "Friedel-Crafts and Related Reactions", Vol. III (Part 1), 1 (1964); Chemical Society of Japan, "Zikkenkagakukoza (Course of Experimental Chemistry)", Vol. 19, 316 (1957); Chemical Society of Japan, "Sin-Zikkenkagakukoza (New Course of Experimental Chemistry)", Vol. 14 (II), 751 (1977)] as well as the methods described in Journal of Organic Chemistry, 11, 444 (1946); ibid., 12, 617 (1947); ibid., 31, 1655 (1966); Journal of the Chemical Society, 1952, 1123, 4162; ibid., 1955, 3417; ibid., 1968C, 2502; ibid., 1971C 3347; Canadian Journal of Chemistry, 41, 2103 (1963), and the like, and those in accordance therewith.

The following Table 1 tabulates physical constants or appearance of some novel compounds out of the aromatic ketones (II).

TABLE I

| | ArCOR$^1$ | |
|---|---|---|
| Ar | R$^1$ | Physical constants or appearance |
| 3-CF$_3$-phenyl | CH$_3$ | b.p., 89° C./15 mmHg |
| 4-CH$_3$S-3-CH$_3$-phenyl | CH$_3$ | b.p., 108–110° C./0.2 mmHg |
| 4-CH$_3$SO-3-CH$_3$-phenyl | CH$_3$ | Oily substance |
| 4-CH$_3$SO$_2$-3-CH$_3$-phenyl | CH$_3$ | Oily substance |
| 4-O$_2$N-3-CH$_3$-phenyl | CH$_3$ | b.p., 73° C. |
| 4-Cl-3,5-(CH$_3$)$_2$-phenyl | CH$_3$ | Solid substance |

TABLE I-continued

| Ar | ArCOR¹ R¹ | Physical constants or appearance |
|---|---|---|
| 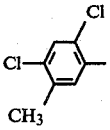 | $CH_3$ | b.p., 150–152° C./20 mmHg |
| 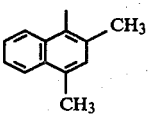 | $CH_3$ | Solid substance |

As to 2-pyrimidylhydrazine represented by the formula (III), many homologues are known in the literature and the others may be synthesized by the known methods described in the literature or those in accordance therewith. For example, they may be easily produced by reacting with hydrazine or mono-lower-alkylhydrazine such as methylhydrazine and ethylhydrazine in the presence of an organic or inorganic base a pyrimidine derivative having in the 2-position a halogen atom such as chlorine and bromine, a lower alkoxyl group such as methoxy and ethoxy, a phenoxyl group, mercapto group, a lower alkylthio group such as methylthio and ethylthio, a phenylthio group, a lower alkylsulfonyl group such as methylsulfonyl and ethylsulfonyl, phenylsulfonyl group, nitroamino group, cyanoamino group, a tri-lower-alkylammonium group such as trimethylammonium and triethylammonium, and others [Yakugaku Zasshi, 73, 159 and 598 (1953); ibid., 79, 1477 (1959); Chemical & Pharmaceutical Bulletin, 17, 1479 (1969); Australian Journal of Chemistry, 30, 2515 (1977)].

Shown in the following Table II are some of physical constants of novel compounds of 2-pyrimidylhydrazine (III):

TABLE II

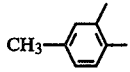

| R² | R³ | R⁴ | R⁵ | Physical constants |
|---|---|---|---|---|
| H | $CH_3$ | $CH_3$ | $CH_3$ | m.p. 165–167° C. |
| H | $CH_3$ | —(CH=CH)₂— | | m.p. 180–181° C. |

As the amidinohydrazone represented by the formula (IV), the non-substituted homologue (Ar=$C_6H_5$; R¹=$CH_3$; R²=H) is the known compound described in the literature, and the others may be produced by the known methods described in the literature or those in accordance therewith. For example, they may be easily synthesized by reacting an aromatic ketone (II) with an aminoguanidine bicarbonate salt or nitrate salt in the presence of an organic or inorganic base. The amidinohydrazone obtained in this manner has the basicity and can therefore be isolated as a salt with an organic or inorganic acid, not to mention a free base. The acid salt may be newly neutralized to be subjected to the reaction according to the present invention as the free base, or subjected to the reaction while it is as the acid salt [Annalen der Chemie, 307, 293 (1899)]. Although it is expected that there exist the Z-form and E-form geographical isomers in relation to the C=N bond of the amidino-hydrazone, meanwhile, the mixture of the isomers without being isolated for indentification or either of these without being characterized is subjected to the reaction according to the present invention.

Shown in the following Table III are some physical constants of the novel compounds of the amidinohydrazone (IV):

TABLE III $$Ar-\underset{\underset{R^1}{|}}{C}=N-\underset{\underset{R^2}{|}}{N}-C\diagup_{NH_2}^{NH}$$

| Ar | R¹ | R² | Physical constants |
|---|---|---|---|
| 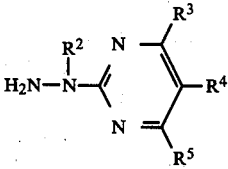 | $CH_3$ | H | m.p. about 160° C. |
| 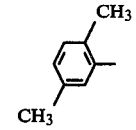 | $CH_3$ | H | m.p. about 125° C. |
| 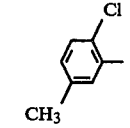 | $CH_3$ | H | m.p. about 174° C. (acetate) |

β-diketones represented by the formula (V) are described in the lists of reagent makers in Japan and abroad and readily available in various kinds. The others may be easily synthesized by the ordinary methods of synthesis of β-diketones, for example, the general method based on alkylation reaction of acetylacetone or those in accordance therewith [H. O. House, "Modern Synthetic Reactions", 2nd ed., 492 and 734 (1972); Chemical Society of Japan (editor), "Zikkenkagakukoza (Course of Experimental Chemistry)", 19, 316 (1957); Chemical Society of Japan, "Sin-Zikkenkagakukoza (New Course of Experimental Chemistry)", 14(II), 751 (1977)] as well as by the methods described in Organic Syntheses, III, 291 (1955); ibid., V. 785 and 848 (1973); Chemical Bulletin of Japan, 88, 1068 (1967); Journal of the American Chemical Society, 68, 453 (1946), etc., and those in accordance therewith.

The pyrimidine derivatives (I) or salts of them according to the present invention possess strong antimicrobial activity against a wide range of plant pathogenic microorganisms, particularly against fungi, and, when they are applied as an antimicrobial agent for paddy field uses, not only exterminate *Pyricularia oryzae* Cavara but also possess the exterminating effect against *Pellicularia sasakii* (Shirai) S. Ito, *Helminthosporium sigmoideum*, *Helminthosporium oryzae*, etc. Furthermore, they have strong antimicrobial activity against not only pathogenic microorganisms of rice plants but also those causing diseases on vegetables and many other crops. For example, they have the antimicrobial activity against *Phytophthora capsici*, *Sclerotinia sclerotiorum* (Libert) deBary, *Botrytis cinerea* etc.

In addition, the compounds (I) or salts of them according to the present invention possess not only the therapeutic capacity of acting, when applied to an already disease-attacked plant, to inhibit the disease expansion, but also the preventive capacity of preventing, when applied on unattacked plants, the infection by a pathogenic agent to protect such plant. As to the application method, they may be applied by spraying to stems and leaves of plants and applied to root portions of plants, whereby they, with their strong penetrating property, are absorbed into the plants, migrating through them to spread widely, and develop the capacity of retaining the concentration necessary for protecting the plants.

The compounds (I) or salts of them, despite their strong antimicrobial activities, are low in skin irritating property and oral toxicity toward warm-blooded animals, and exercise reduced effect on the environment, for example in terms of fish toxicity, etc. Furthermore, they exhibit phytotoxic action against a variety of plants, not at all or merely slight, and affect in no way subsequent growths and crop yields. This is assumed to be ascribed to the fact that the compounds (I) or salts of them have the strong affinity toward plants and a proper degree of chemical stability. In other words, they are assumed to be gradually inactivated through hydrolysis of the hydrazone linkage contained in the molecules. It may be said, consequently, that the pyrimidine derivatives (I) or salts of them according to the present invention are provided with the highly superior nature and property as antimicrobial agents for multipurpose, agricultural uses.

The antimicrobial agent according to the present invention may consist of two or more kinds of the compounds of the formula (I) or salts of them in combination, not to mention one kind thereof. The antimicrobial agent may comprise a free base of, or an organic or inorganic acid salt of, the compounds (I) or salts of them of the present invention (hereinafter referred to as the active component), solely or in conjunction with a variety of natural materials, additives, solvents, etc. being added, as occasion needs. Referring in more particular to this, the active component may be used as a solid, as it is, for the purpose of retaining its effectiveness for a prolonged period of time, or may be dissolved or dispersed in a suitable liquid carrier (for example, a solvent), or admixed with or absorbed on an appropriate solid carrier (for example, a diluent or an extender), followed by further adding an emulsifying agent, dispersing agent, suspending agent, spreader, penetrant, wetting agent, thickening agent, stabilizer, etc., to thus use as an oil preparation, emulsifiable concentrate, wettable powder, aqueous solution, suspension, dust, granules, fine granules, tablet, spray, and other suitable preparation forms.

Usable as such solvent may be water, alcohols (e.g. methyl alcohol, ethyl alcohol, ethyleneglycol, propyleneglycol, etc.), ketones (e.g., acetone, methyl ethyl ketone, etc.), ethers (e.g., dioxane, tetrahydrofurane, cellosolve, etc.), aliphatic hydrocarbons (e.g., gasoline, kerosene, light oil, fuel oil, machine oil, etc.), aromatic hydrocarbons (e.g., benzene, toluene, xylene, solvent naphtha, methylnaphthalene, etc.) and other organic bases (e.g., pyridine, aldehyde collidine, etc.), halogenated hydrocarbons (e.g., chloroform, carbon tetrachloride, etc.), acid amides (e.g., dimethylformamide), esters (e.g., ethyl acetate, butyl acetate, glycerine esters of fatty acids, etc.) and nitriles (e.g., acetonitrile), sulfur-containing compounds (e.g., dimethylsulfoxide, tetramethylene sulfone, etc.), and the like.

Operable as the solid carrier such as diluent and extender may be, for example, powder of plant origin (e.g., rice bran, soybean powder, tobacco powder, wheat flour, wood powder, etc.), powder of mineral origin (e.g., kaolin, bentonite, calcium phosphate, clays such as acid clay, talcs such as talck powder and pagotite powder, silicas such as diatomaceous earth and mica powder, etc.), and alumina, sulfur powder, activated carbon, etc., which may be used solely or as a mixture of not less than two kinds.

The emulsifying agent, spreader, penetrant, dispersing agent and the like, which are usable, include soaps, sulfates of higher alcohols, alkyl sulfonic acid, alkyl aryl sulfonic acid, quarternary ammonium salt, oxyalkylamine, fatty acid ester, surface active agents based on polyalkylene oxide, anhydrosorbitol, etc., and the like, which are preferably incorporated into preparations, generally at a level of 0.2 to 10%. Further, casein, gelatin, starch, arginic acid, agar, CMC, polyvinyl alcohol, pine oil, rice bran oil, bentonite, cresol soap, etc. may be used, if desired. In addition, suitably mixed, as occasion demands, may be different kinds of fungicides and bactericides (e.g., organic chlorine fungicides, organic phosphorus fungicides, benzimidazole fungicides, copper fungicides, organic sulfur fungicides, phenol fungicides, antibiotics, etc.), insecticides (e.g., natural insecticides, carbamate insecticides, organic phosphorus insecticides, etc.) and others such as miteicides, nematocides, herbicides, plant growth regulators, stabilizers, synergists, attractants, repellent, perfumes, plant nutrients, fertilizers, various amino acids, low-molecular or high-molecular-weight phosphoric acid salts, etc., while metal salts may be added for the purpose of strengthening the effectiveness.

Content of the active component in antimicrobial agents for control uses according to the present invention may suitably be in the range of 10 to 90% for emulsifiable concentrate, wettable powder, etc., 0.1 to 10% for oil preparation, dust, etc., and 5 to 50% for granules.

Meanwhile, the emulsifiable concentrate, wettable powder, etc., in bringing into practical use, may be suitably diluted with water, etc. (for example, up to 50 to 5000 times) to be sprayed.

Used amount of the active component, mixing combination thereof with other kinds of antimicrobial agents and formulation ratio for these, etc. vary depending upon the growing phase of the plant to be treated, its growth condition, species of diseases, condition of disorders, application time or method for antimicrobial agent, and other conditions, and may generally be adjusted in such a way that the active component may be at an application rate within the range of 10 to 300 g per 10 are. The application concentration may be in the range of 10 to 1000 ppm of the active component, while the application method may be by means of spraying, dusting and irrigating on crops or dust coating of seeds; and, any application method, only if it secures the safe and effective application on crops, shall not impose any restriction on the present invention, no matter what the used amount, application concentration and application method may be.

The antimicrobial agent for plant disease controlling uses according to the present invention has the reduced sideeffect and can achieve the superior action and effectiveness by a simple procedure, at reduced costs, and to a precise degree, thus offerring the very great usefulness to the relevant business circles.

In the specification, the following abbreviations are used; "ml"=milliliter, "nM"=millimol, "mg"=milligram, "g"=gram, "μg"=microgram, "mm"=millimeter, "cm"=centimeter, "a"=are, "%"=percent, "NMR"=Nuclear Magnetic Resonance, "S"=singlet, "ppm"=part per million, "comp."=Compound, "No."=Number, "Synth."=Synthesis, "Phys."=Physical, "ca"=circa, "m.p."=melting point, "Concn."=Concentration.

The Examples and Test Examples are as follows:

EXAMPLE 1

To 15 ml of ethanol are added 1.50 g (9 mM) of o-methylthioacetophenone (II: Ar=o-$CH_3S.C_6H_4$; $R^1$=$CH_3$) and 1.38 g (10 mM) of 2-hydrazino-4,6-dimethylpyrimidyl (III: $R^2$=$R^4$=H; $R^3$=$R^5$=$CH_3$), followed by boiling under reflux for about 13 hours. After the reaction, the reaction mixture is concentrated under reduced pressure, and the resultant viscous, oily substance is chromatographed on a column (silica gel/chloroform) whereby, since the Z-form of 4,6-dimethyl-2-[1-(2-methylthiophenyl)ethylidenehydrazino]pyrimidine is eluted first, along with the E-form then after a slight time interval, by elution of both isomers with chloroform, the elution fractions containing the same isomer are collected by checking by way of thin-layer chromatography, followed by concentrating each of them to yield the isomers as a crystalline solid, respectively.

Z-form:
Yield; 0.95 g (38%). Melting point; 125°–127° C.
Elementary analysis ($C_{15}H_{18}N_4S$):

|  | C | H | N |
| --- | --- | --- | --- |
| Calcd. (%): | 62.90 | 6.33 | 19.56 |
| Found (%): | 62.80 | 6.40 | 19.59 |

NMR ($CDCl_3$, ppm), δ value.
Pyrimidine 4,6-$CH_3$: 2.33 (6H, s.), N=C—$CH_3$, $SCH_3$: 2.35 (3H, s.), 2.43 (3H, s.).
Pyrimidine 5-H: 6.46 (1H, s.), phenyl proton: 7.0–7.5 (4H, m.), NH: 7.88 (1H, s.).

E-form:
Yield; 1.20 g (48%), melting point; 94° C.
Elementary analysis ($C_{15}H_{18}N_4S$):

|  | C | H | N |
| --- | --- | --- | --- |
| Calcd. (%): | 62.90 | 6.33 | 19.56 |
| Found (%): | 62.85 | 6.23 | 19.46 |

NMR ($CDCl_3$, ppm), δ value.
Pyrimidine 4,6-$CH_3$: 2.35 (6H, s.), N=C-$CH_3$, $SCH_3$: 2.30 (3H, s.), 2.41 (3H, s.).
Pyrimidine 5-H: 6.51 (1H, s.), phenyl proton: 7.0–7.5 (4H, m.), NH; 8.25 (1H, s.).

EXAMPLE 2

A 2.00 g (10 mM) portion of 2-(2,4-dimethylphenyl)ethylideneaminoguanidine (IV: Ar=2.4-$(CH_3)_2C_6H_3$; $R^1$=$CH_3$; $R^2$=H) and 2.90 g (23 mM) of 3-ethylacetylacetone (V: $R^3$=$R^5$=$CH_3$; $R^4$=$C_2H_5$) are stirred for about 3.5 hours, while keeping them at 130° to 140° C. in an oil bath. After the reaction, an excessive amount of β-diketone is distilled off under reduced pressure, and the resultant viscous, oily substance is chromatographed on a column (silica gel/ethyl acetate+n-hexane), whereby, since the Z-form of 5-ethyl-4,6-dimethyl-2-[1-(2,4-dimethylphenyl)ethylidenehydrazino]-pyrimidine is first eluted, with the E-form successively eluted partly in a mixture with the Z-form, by elution of both isomers with a mixed solvent of ethyl acetate and n-hexane, the elution fractions containing the same isomer are collected by checking by means of thin-layer chromatography, followed by concentrating each of them to give the Z-form as a crystalline solid and the E-form as a viscous oily substance.

Z-form:
Yield; 1.50 g (51%), melting point; 127°–129° C.
Elementary analysis ($C_{18}H_{24}N_4$):

|  | C | H | N |
| --- | --- | --- | --- |
| Calcd. (%): | 72.93 | 8.16 | 18.90 |
| Found (%): | 72.35 | 8.09 | 18.72 |

NMR ($CDCl_3$, ppm), δ value.
NH: 7.72 (1H, s.).
E-form (mixed with Z-form):
Yield; 0.70 g (24%). Viscous, oily substance.
Elementary analysis ($C_{18}H_{24}N_4$):

|  | C | H | N |
| --- | --- | --- | --- |
| Calcd. (%): | 72.93 | 8.16 | 18.90 |
| Found (%): | 72.78 | 7.99 | 18.48 |

NMR ($CDCl_3$, ppm), δ value.
NH: 7.75 & 8.08 (ratio of Z-form: E-form=1:2).

EXAMPLE 3

The compounds Nos. 1 through 126, as described hereinafter, are produced in the same manner as in Example 1 (Synthesis method A) or in Example 2 (Synthesis method B), and tabulated in the following Table are their chemical structures (Ar, $R^1$, $R^2$, $R^3$, $R^4$, $R^5$), synthesis method and physical constants (appearance), inclusive of the compounds obtained in Examples 1 and 2, whereby, in the column, (ratio of Z:E) of the Table, E stands for the E-form solely obtained and Z for the Z-form solely, while Z+E stands for a mixture of both isomers, with their ratio unidentified; the compound No. 115, with Ar and R' being the same, has no structural isomer and can be isolated by merely concentrating after the reaction.

| Comp. No. | Ar | $R^1$ | $R^2$ | $R^3$ | $R^4$ | $R^5$ | Ratio of Z:E | Synth. method | Phys. constants (appearance) |
| --- | --- | --- | --- | --- | --- | --- | --- | --- | --- |
| 1 | $C_6H_5$ | $CH_3$ | H | $CH_3$ | H | $CH_3$ | E | A | m.p. 89–91° C. |
| 2 | O—$CH_3.C_6H_4$ | $CH_3$ | H | $CH_3$ | H | $CH_3$ | Z | A | m.p. 178–180° C. |
| 3 | O—$CH_3.C_6H_4$ | $CH_3$ | H | $CH_3$ | H | $CH_3$ | E | A | m.p. 110–111° C. |
| 4 | m-$CH_3.C_6H_4$ | $CH_3$ | H | $CH_3$ | H | $CH_3$ | E | A | m.p. 85–88° C. |
| 5 | p-$CH_3.C_6H_4$ | $CH_3$ | H | $CH_3$ | H | $CH_3$ | E | A | m.p. 164–166° C. |

-continued

| Comp. No. | Ar | R¹ | R² | R³ | R⁴ | R⁵ | Ratio of Z:E | Synth. method | Phys. constants (appearance) |
|---|---|---|---|---|---|---|---|---|---|
| 6 | O—CH₃O.C₆H₄ | CH₃ | H | CH₃ | H | CH₃ | E | A | m.p. 128° C. |
| 7 | O—CH₃S.C₆H₄ | CH₃ | H | CH₃ | H | CH₃ | Z | A | m.p. 125–127° C. |
| 8 | O—CH₃S.C₆H₄ | CH₃ | H | CH₃ | H | CH₃ | E | A | m.p. 94° C. |
| 9 | O—Cl.C₆H₄ | CH₃ | H | CH₃ | H | CH₃ | E | A | m.p. 132° C. |
| 10 | m-Cl.C₆H₄ | CH₃ | H | CH₃ | H | CH₃ | E | A | m.p. 110° C. |
| 11 | p-Cl.C₆H₄ | CH₃ | H | CH₃ | H | CH₃ | E | A | m.p. 166–168° C. |
| 12 | O—F.C₆H₄ | CH₃ | H | CH₃ | H | CH₃ | E | A | m.p. 132–134° C. |
| 13 | O—Br.C₆H₄ | CH₃ | H | CH₃ | H | CH₃ | E | A | m.p. 129–131° C. |
| 14 | O—I.C₆H₄ | CH₃ | H | CH₃ | H | CH₃ | E | A | m.p. 138–139° C. |
| 15 | O—NO₂.C₆H₄ | CH₃ | H | CH₃ | H | CH₃ | E | A | m.p. 144–145° C. |
| 16 | O—CF₃.C₆H₄ | CH₃ | H | CH₃ | H | CH₃ | E | A | m.p. 123–125° C. |
| 17 | 2,4-(CH₃)₂.C₆H₃ | CH₃ | H | CH₃ | H | CH₃ | Z | A | m.p.ca. 99° C. |
| 18 | 2,4-(CH₃)₂.C₆H₃ | CH₃ | H | CH₃ | H | CH₃ | 3:5 | A | (viscous oil) |
| 19 | 2,5-(CH₃)₂.C₆H₃ | CH₃ | H | CH₃ | H | CH₃ | Z | A | m.p.ca. 99° C. |
| 20 | 2,5-(CH₃)₂.C₆H₃ | CH₃ | H | CH₃ | H | CH₃ | 3:5 | A | (viscous oil) |
| 21 | 3,4-(CH₃)₂.C₆H₃ | CH₃ | H | CH₃ | H | CH₃ | E | A | m.p. 144–146° C. |
| 22 | 2,4-(Et)₂.C₆H₃ | CH₃ | H | CH₃ | H | CH₃ | 2:1 | A | (viscous oil) |
| 23 | 2,5-(Et)₂.C₆H₃ | CH₃ | H | CH₃ | H | CH₃ | 1:2 | A | (viscous oil) |
| 24 | 2,4-(i-C₃H₇)₂.C₆H₃ | CH₃ | H | CH₃ | H | CH₃ | 2:3 | A | (viscous oil) |
| 25 | 2,5-(i-C₃H₇)₂.C₆H₃ | CH₃ | H | CH₃ | H | CH₃ | 1:1 | A | (viscous oil) |
| 26 | 2-CH₃—5-Et.C₆H₃ | CH₃ | H | CH₃ | H | CH₃ | 1:1 | A | (viscous oil) |
| 27 | 2-CH₃—5-n-C₃H₇.C₆H₃ | CH₃ | H | CH₃ | H | CH₃ | 1:1 | A | (viscous oil) |
| 28 | 2-CH₃—5-i-C₃H₇.C₆H₃ | CH₃ | H | CH₃ | H | CH₃ | 3:1 | A | (viscous oil) |
| 29 | 2-CH₃—5-t-C₄H₉.C₆H₃ | CH₃ | H | CH₃ | H | CH₃ | 1:2 | A | (viscous oil) |
| 30 | 2,4-Cl₂.C₆H₃ | CH₃ | H | CH₃ | H | CH₃ | E | A | m.p. 175–176.5° C. |
| 31 | 2,5-Cl₂.C₆H₃ | CH₃ | H | CH₃ | H | CH₃ | E | A | m.p. 165–166° C. |
| 32 | 3,4-Cl₂.C₆H₃ | CH₃ | H | CH₃ | H | CH₃ | E | A | m.p. 148–149° C. |
| 33 | 2-CH₃—4-CH₃O.C₆H₃ | CH₃ | H | CH₃ | H | CH₃ | 1:1 | A | (viscous oil) |
| 34 | 2-CH₃—4-CH₃S.C₆H₃ | CH₃ | H | CH₃ | H | CH₃ | 3:1 | A | (viscous oil) |
| 35 | 2-CH₃—4-CH₃SO.C₆H₃ | CH₃ | H | CH₃ | H | CH₃ | 3:1 | A | m.p. 135° C. |
| 36 | 2-CH₃—4-CH₃SO₂.C₆H₃ | CH₃ | H | CH₃ | H | CH₃ | E | A | m.p.ca. 210° C. |
| 37 | 2-CH₃—4-Cl.C₆H₃ | CH₃ | H | CH₃ | H | CH₃ | E | A | m.p.ca. 158° C. |
| 38 | 2-CH₃—4-Cl.C₆H₃ | CH₃ | H | CH₃ | H | CH₃ | 1:1 | A | (viscous oil) |
| 39 | 2-CH₃—4-NO₂.C₆H₃ | CH₃ | H | CH₃ | H | CH₃ | E | A | m.p. 170–172° C. |
| 40 | 2-Cl—5-CH₃.C₆H₃ | CH₃ | H | CH₃ | H | CH₃ | E | A | m.p. 155–157° C. |
| 41 | 2-Cl—5-CH₃.C₆H₃ | CH₃ | H | CH₃ | H | CH₃ | 6:1 | A | m.p.ca. 125° C. |
| 42 | 2-Cl—5-CH₃O.C₆H₃ | CH₃ | H | CH₃ | H | CH₃ | 1:2 | A | m.p.ca. 98° C. |
| 43 | 2-Br—5-CH₃.C₆H₃ | CH₃ | H | CH₃ | H | CH₃ | 3:4 | A | m.p.ca. 110° C. |
| 44 | 2-Br—5-CH₃O.C₆H₃ | CH₃ | H | CH₃ | H | CH₃ | E | A | m.p.ca. 142° C. |
| 45 | 2,4,5-(CH₃)₃.C₆H₂ | CH₃ | H | CH₃ | H | CH₃ | Z | A | m.p.ca. 112° C. |
| 46 | 2,4,5-(CH₃)₃.C₆H₂ | CH₃ | H | CH₃ | H | CH₃ | E | A | m.p. 159–160° C. |
| 47 | 2,3,4-Cl₃.C₆H₂ | CH₃ | H | CH₃ | H | CH₃ | E | A | m.p. 225° C. |
| 48 | 2,4-(CH₃)₂—5-Et.C₆H₂ | CH₃ | H | CH₃ | H | CH₃ | 2:1 | A | (viscous oil) |
| 49 | 2,5-(CH₃)₂—4-Cl.C₆H₂ | CH₃ | H | CH₃ | H | CH₃ | Z | A | m.p.ca. 130° C. |
| 50 | 2-CH₃—4,5-Cl₂.C₆H₂ | CH₃ | H | CH₃ | H | CH₃ | 5:1 | A | m.p.ca. 150° C. |
| 51 | 2,4-Cl₂—5-CH₃.C₆H₂ | CH₃ | H | CH₃ | H | CH₃ | E | A | m.p.ca. 204–205° C. |
| 52 | 2,4-Cl₂—5-CH₃.C₆H₂ | CH₃ | H | CH₃ | H | CH₃ | 2:5 | A | m.p.ca. 196° C. |
| 53 | 2,3,4,5-(CH₃)₄.C₆H | CH₃ | H | CH₃ | H | CH₃ | 5:3 | A | m.p.ca. 116° C. |
| 54 | α-C₁₀H₇ | CH₃ | H | CH₃ | H | CH₃ | E | A | m.p. 161–163° C. |
| 55 | 2,4-(CH₃)₂—α-C₁₀H₅ | CH₃ | H | CH₃ | H | CH₃ | 1:5 | A | m.p.ca. 172° C. |
| 56 | 2,6-(CH₃)₂—α-C₁₀H₅ | CH₃ | H | CH₃ | H | CH₃ | Z | A | m.p.ca. 168° C. |
| 57 | 2,6-(CH₃)₂—α-C₁₀H₅ | CH₃ | H | CH₃ | H | CH₃ | 1:3 | A | (viscous oil) |
| 58 | 6,7-(CH₃)₂—α-C₁₀H₅ | CH₃ | H | CH₃ | H | CH₃ | Z | A | m.p. 149–151° C. |
| 59 | 6,7-(CH₃)₂—α-C₁₀H₅ | CH₃ | H | CH₃ | H | CH₃ | E | A | m.p.ca. 199° C. |
| 60 | β-C₁₀H₇ | CH₃ | H | CH₃ | H | CH₃ | E | A | m.p. 130–133° C. |
| 61 | β-C₁₀H₇ | CH₃ | H | CH₃ | H | CH₃ | E | A | m.p. 129–131° C. (acetate) |
| 62 | 1,4-(CH₃)₂—β-C₁₀H₅ | CH₃ | H | CH₃ | H | CH₃ | Z | A | m.p.ca. 169° C. |
| 63 | 1,4-(CH₃)₂—β-C₁₀H₅ | CH₃ | H | CH₃ | H | CH₃ | E | A | m.p.ca. 208–210° C. |
| 64 | 5,8-(CH₃)₂—β-C₁₀H₅ | CH₃ | H | CH₃ | H | CH₃ | E | A | m.p. 170–172° C. |
| 65 | O—CH₃.C₆H₄ | CH₃ | CH₃ | CH₃ | H | CH₃ | E | A | (viscous oil) |
| 66 | 2,4-(CH₃)₂.C₆H₃ | CH₃ | H | CH₃O | H | CH₃ | E | A | m.p. 173–175° C. |
| 67 | O—CH₃.C₆H₄ | CH₃ | H | CH₃ | —(CH=CH)₂— | | Z + E | A | (viscous oil) |
| 68 | 2,4-(CH₃)₂.C₆H₃ | CH₃ | H | CH₃ | —(CH=CH)₂— | | Z + E | A | m.p.ca. 143° C. |
| 69 | 2,5-(CH₃)₂.C₆H₃ | CH₃ | H | CH₃ | —(CH=CH)₂— | | Z + E | A | (viscous oil) |
| 70 | 2-Cl—5-CH₃.C₆H₃ | CH₃ | H | CH₃ | —(CH=CH)₂— | | Z + E | A | m.p.ca. 80° C. |
| 71 | O—CH₃.C₆H₄ | CH₃ | H | CH₃ | CH₃ | CH₃ | 3:4 | A | m.p.ca. 100° C. |
| 72 | 2,5-(CH₃)₂.C₆H₃ | CH₃ | H | CH₃ | CH₃ | CH₃ | 1:1 | B | m.p.ca. 125° C. |
| 73 | 2,5-(CH₃)₂.C₆H₃ | CH₃ | H | CH₃ | Et | CH₃ | 1:1 | B | (viscous oil) |
| 74 | 2,4-(CH₃)₂.C₆H₃ | CH₃ | H | CH₃ | CH₃ | CH₃ | 3:2 | B | m.p. 140° C. |
| 75 | 2,4-(CH₃)₂.C₆H₃ | CH₃ | H | CH₃ | Et | CH₃ | Z | B | m.p. 127–129° C. |
| 76 | 2,4-(CH₃)₂.C₆H₃ | CH₃ | H | CH₃ | Et | CH₃ | 1:2 | B | (viscous oil) |
| 77 | 2,4-(CH₃)₂.C₆H₃ | CH₃ | H | CH₃ | n-Pr | CH₃ | Z | B | m.p.ca. 144° C. |
| 78 | 2,4-(CH₃)₂.C₆H₃ | CH₃ | H | CH₃ | n-Bu | CH₃ | 2:1 | B | m.p.ca. 117° C. |
| 79 | 2,4-(CH₃)₂.C₆H₃ | CH₃ | H | CH₃ | i-Bu | CH₃ | 1:1 | B | m.p.ca. 122° C. |
| 80 | 2,4-(CH₃)₂.C₆H₃ | CH₃ | H | CH₃ | allyl | CH₃ | 1:2 | B | (viscous oil) |
| 81 | 2,4-(CH₃)₂.C₆H₃ | CH₃ | H | CH₃ | H | Et | E | B | m.p. 112–114° C. |
| 82 | 2,4-(CH₃)₂.C₆H₃ | CH₃ | H | Et | H | Et | 5:4 | B | (viscous oil) |
| 83 | 2,4-(CH₃)₂.C₆H₃ | CH₃ | H | n-Pr | H | n-Pr | 3:2 | B | (viscous oil) |

-continued

| Comp. No. | Ar | R¹ | R² | R³ | R⁴ | R⁵ | Ratio of Z:E | Synth. method | Phys. constants (appearance) |
|---|---|---|---|---|---|---|---|---|---|
| 84 | 2,4-(CH₃)₂.C₆H₃ | CH₃ | H | i-Pr | H | i-Pr | 3:5 | B | (viscous oil) |
| 85 | 2,4-(CH₃)₂.C₆H₃ | CH₃ | H | t-Bu | H | t-Bu | 3:2 | B | (viscous oil) |
| 86 | 2,4-(CH₃)₂.C₆H₃ | CH₃ | H | CH₃ | —(CH₂)₃— | | Z + E | B | m.p. 118–120° C. |
| 87 | 2,4-(CH₃)₂.C₆H₃ | CH₃ | H | CH₃ | —(CH₂)₄— | | 1:2 | B | (viscous oil) |
| 88 | 2-Cl—5-CH₃.C₆H₃ | CH₃ | H | CH₃ | CH₃ | CH₃ | 1:1 | B | m.p.ca. 137° C. |
| 89 | 2-Cl—5-CH₃.C₆H₃ | CH₃ | H | CH₃ | Et | CH₃ | E | B | m.p. 129–131° C. |
| 90 | 2-Cl—5-CH₃.C₆H₃ | CH₃ | H | CH₃ | n-Pr | CH₃ | 1:1 | B | (viscous oil) |
| 91 | 2-Cl—5-CH₃.C₆H₃ | CH₃ | H | CH₃ | n-Bu | CH₃ | E | B | m.p.ca. 80° C. |
| 92 | 2-Cl—5-CH₃.C₆H₃ | CH₃ | H | CH₃ | i-Bu | CH₃ | E | B | m.p.ca 132° C. |
| 93 | 2-Cl—5-CH₃.C₆H₃ | CH₃ | H | CH₃ | allyl | CH₃ | E | B | m.p. 126–128° C. |
| 94 | 3-Cl—5-CH₃.C₆H₃ | CH₃ | H | CH₃ | H | Et | E | B | m.p.ca. 95° C. |
| 95 | 2-Cl—5-CH₃.C₆H₃ | CH₃ | H | Et | H | Et | E | B | m.p.ca. 130° C. |
| 96 | 2-Cl—5-CH₃.C₆H₃ | CH₃ | H | n-Pr | H | n-Pr | 1:1 | B | (viscous oil) |
| 97 | 2-Cl—5-CH₃.C₆H₃ | CH₃ | H | i-Pr | H | i-Pr | 3:5 | B | (viscous oil) |
| 98 | 2-Cl—5-CH₃.C₆H₃ | CH₃ | H | t-Bu | H | t-Bu | 1:1 | B | (viscous oil) |
| 99 | 2-Cl—5-CH₃.C₆H₃ | CH₃ | H | CH₃ | —(CH₂)₃— | | E | B | m.p. 143–145° C. |
| 100 | 2-Cl—5-CH₃.C₆H₃ | CH₃ | H | CH₃ | —(CH₂)₄— | | 1:1 | B | (viscous oil) |
| 101 | C₆H₅ | Et | H | CH₃ | H | CH₃ | 3:1 | A | (viscous oil) |
| 102 | O—Cl.C₆H₄ | Et | H | CH₃ | H | CH₃ | E | A | m.p. 106–108° C. |
| 103 | 2,4-(CH₃)₂.C₆H₃ | Et | H | CH₃ | H | CH₃ | Z | A | m.p. 113–115° C. |
| 104 | 2,4-(CH₃)₂.C₆H₃ | Et | H | CH₃ | H | CH₃ | 2:1 | A | m.p.ca. 95° C. |
| 105 | 2,6-(CH₃)₂—α-C₁₀H₅ | Et | H | CH₃ | H | CH₃ | 1:1 | A | (viscous oil) |
| 106 | C₆H₅ | n-Pr | H | CH₃ | H | CH₃ | E | A | m.p. 98–101° C. |
| 107 | 2,4-(CH₃)₂.C₆H₅ | n-Pr | H | CH₃ | H | CH₃ | 1:1 | A | (viscous oil) |
| 108 | 2,4-(CH₃)₂.C₆H₃ | i-Pr | H | CH₃ | H | CH₃ | 3:1 | A | (viscous oil) |
| 109 | P—Cl.C₆H₅ | cyclopropyl | H | CH₃ | H | CH₃ | E | A | m.p.ca. 128° C. |
| 110 | C₆H₅ | CF₃ | H | CH₃ | H | CH₃ | E | A | m.p.ca 132° C. |
| 111 | C₆H₅ | CO₂Et | H | CH₃ | H | CH₃ | E | A | m.p. 127–128° C. |
| 112 | P—Cl.C₆H₄ | CO₂Et | H | CH₃ | H | CH₃ | E | A | m.p. 155–157° C. |
| 113 | 2,4-Cl₂.C₆H₃ | CO₂Et | H | CH₃ | H | CH₃ | Z | A | m.p. 173–176° C. |
| 114 | 2,4-Cl₂.C₆H₃ | CO₂Et | H | CH₃ | H | CH₃ | E | A | m.p.ca. 197° C. |
| 115 | C₆H₅ | C₆H₅ | H | CH₃ | H | CH₃ | — | A | m.p.ca. 175° C. |
| 116 | O—Cl.C₆H₄ | p-Cl.C₅H₄ | H | CH₃ | H | CH₃ | Z + E | A | m.p. 194–197° C. |
| 117 | C₆H₅ | C₆H₅—CH₂ | H | CH₃ | H | CH₃ | Z + E | A | (viscous oil) |
| 118 | O—Et.C₆H₄ | CH₃ | H | CH₃ | H | CH₃ | 1:9 | A | m.p. 117–119° C. |
| 119 | 2,4,6-(CH₃)₃.C₆H₂ | CH₃ | H | CH₃ | H | CH₃ | E | A | m.p. 186–189° C. |
| 120 | 2,4,6-(CH₃)₃.C₆H₂ | CH₃ | H | CH₃ | H | CH₃ | Z | A | (viscous oil) |
| 121 | 2,4-(CH₃)₂.C₆H₃ | CH₃ | H | CH₃ | H | H | Z + E | A | (viscous oil) |
| 122 | 2,4-(CH₃)₂.C₆H₃ | CH₃ | H | H | H | H | E | A | m.p.ca. 125° C. |
| 123 | 2,6-Cl₂.C₆H₃ | CH₃ | H | CH₃ | H | CH₃ | Z + E | A | m.p.ca. 135° C. |
| 124 | O—(CH₃)₂N.C₆H₄ | CH₃ | H | CH₃ | H | CH₃ | Z + E | A | m.p.ca. 140° C. |
| 125 | O—CH₃.C₆H₄ | CH₃ | H | CH₃ | H | H | 1:1 | A | m.p.ca. 76° C. |
| 126 | O—Cl.C₆H₄ | CH₃ | H | CH₃ | CH₃ | CH₃ | Z + E | A | m.p.ca. 110° C. |

Remarks: Et = —C₂H₅,
Pr = —C₃H₇,
Bu = —C₄H₉

EXAMPLE 4

The wettable powder, comprising 50% of the compound (3), 2% of sodium lignin sulfonate, 3% of white carbon, 5% of polyoxyethylene alkylaryl ether and 40% of clay being mixed. It is diluted with water to 1000 to 3000 times, and sprayed at an application rate of 10 to 20 l per 1 are.

EXAMPLE 5

The dust, comprising 3% of the compound (9), 0.1% of aluminium stearate and 96.9% of clay being mixed. It is dusted at an application rate of 300 to 500 g per 1 are.

EXAMPLE 6

The granule, comprising 5% of the compound (18), 5% of gum arabic, 30% of bentonite and 60% of talc being mixed and granulated. It is directly applied at an application rate of 300 g to 500 g per 1 are.

EXAMPLE 7

The emulsifiable concentrate, containing 20% of the compound (20), 75% of xylene and 5% of polyoxyethylene alkylaryl ether. It is diluted with water to 40 to 2000 times and directly applied at an application rate of 10 l per 1 are.

EXAMPLE 8

The wettable powder, comprising 30% of the compound (38), 5% of sodium lignin sulfonate, 5% of polyoxyethylene alkylaryl ether and 60% of clay being mixed and pulverized. It is diluted with water to 40 to 2000 times and directly applied at an application rate of 10 l per 1 are.

EXAMPLE 9

The granule, comprising a mixture composed of 10% of the compound (41), 5% of sodium lignin sulfonate and 85% of bentonite being kneaded with water and granulated. It is directly applied at an application rate of 300 to 500 g per 1 are.

TEST EXAMPLE 1

By means of a multiple dilution method with the use of an agar medium, in accordance with the procedure as outlined below, the antimicrobial activity test is carried out on the representative, objective compounds of the present invention (indicated by the compound number as described in Example 3) as well as the control reference compound, with the test results as tabulated in the table below given.

(1) Assay medium

A glucose-bouillion agar medium or potato sucrose agar medium (employed merely for the test microorganism No. 5)

(2) Preparation of antimicrobial agents

A 40 mg portion of the test compound is dissolved in a mixture of 0.5 ml of N,N-dimethylformamide and 9.5 ml of acetone, and diluted with sterilized water to a concentration of 1000 µg/ml (the concentration in the media is 1/10).

(3) Test microorganisms (1) *Pyricularia oryzae* IFO 5279, the fungus causing the rice blast.

(2) *Helminthosporium sigmoideum* IFO 4867, the fungus causing stem rot of rice.

(3) *Helminthosporium oryzae*, the fungus causing Helmithosporium leaf spot of rice.

(4) *Pellicularia sasakii* IFO 6330, the fungus causing the sheath blight of rice.

(5) *Phytophthora capsici* IFO 8386, the fungus causing downy mildew of cucumber.

(6) *Botrytis cinerea*, the pathogen of gray mold of strawberry.

(7) *Sclerotinia sclerotiorum* IFO 4876, the pathogen of Sclerotinia rot.

(4) Control reference compound

The compound as described in Example 2 of Japanese Published unexamined patent application No. 12786/1978; and Chemical Abstracts, Vol. 89, 1978, page 642, 89:43476q;

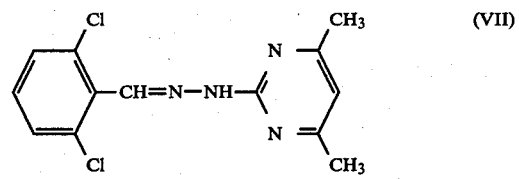

(5) Inoculation

The media are inoculated with pieces of agars with hyphae, for the test microorganism Nos. 4, 5 and 6, while being inoculated by painting bacterial fluids for the others.

(6) Incubation

Incubation is performed at 28° C. for 4 days, for the test microorganism Nos. 1, 2 and 6, at 28° C. for 3 days for the test microorganism Nos. 3,4 and 7, and at 28° C. for 5 to 6 days for the test microorganism No. 5.

(7) Estimation

The minimum inhibitory concentrations (MIC, µg/ml) are determined.

| Comp. No. | Kinds of the test microorganisms ||||||||
|---|---|---|---|---|---|---|---|
| | 1 | 2 | 3 | 4 | 5 | 6 | 7 |
| 2 | 3.12 | 1.56 | 25 | 50 | 3.12 | 25 | 50 |
| 3 | 0.78 | 0.39 | 6.25 | 12.5 | 3.12 | 6.25 | 1.56 |
| 7 | 3.12 | 0.78 | >100 | 100 | 1.56 | 50 | 50 |
| 8 | 0.2 | 0.2 | 12.5 | 25 | 1.56 | 6.25 | 6.25 |
| 9 | 0.39 | 0.78 | 6.25 | 12.5 | 6.25 | 12.5 | 6.25 |
| 13 | 0.78 | 0.78 | 6.25 | >100 | 12.5 | 12.5 | 6.25 |
| 15 | 1.56 | 0.78 | 50 | 100 | 6.25 | 50 | 25 |
| 16 | 0.78 | 0.78 | 100 | 50 | 12.5 | 12.5 | 25 |
| 17 | 1.56 | 6.25 | 25 | 25 | 12.5 | 25 | 12.5 |
| 18 | 1.56 | 0.78 | 25 | 12.5 | 12.5 | 6.25 | 6.25 |
| 19 | 1.56 | 1.56 | 25 | 50 | 12.5 | 25 | 12.5 |
| 20 | 0.78 | 0.78 | 25 | 12.5 | 12.5 | 6.25 | 6.25 |
| 22 | 0.78 | 0.2 | 25 | 100 | 100 | 12.5 | 6.25 |
| 23 | 0.39 | 0.2 | >100 | 25 | 50 | 12.5 | 6.25 |
| 26 | 0.78 | 0.39 | 12.5 | 12.5 | 12.5 | 12.5 | 6.25 |
| 27 | 0.39 | 0.39 | 12.5 | 50 | >100 | 25 | 6.25 |
| 28 | 0.78 | 0.39 | 50 | >100 | >100 | 25 | 6.25 |
| 31 | 0.2 | 0.1 | 25 | >100 | 25 | 50 | 3.12 |
| 34 | 1.56 | 6.25 | 12.5 | 12.5 | 25 | 6.25 | 3.12 |
| 37 | 0.2 | 0.2 | 6.25 | 12.5 | 3.12 | 6.25 | 1.56 |
| 38 | 0.39 | 0.39 | 6.25 | 12.5 | 6.25 | 6.25 | 3.12 |
| 40 | 0.39 | 0.2 | 12.5 | 25 | 6.25 | 6.25 | 3.12 |
| 41 | 0.56 | 0.78 | 25 | 100 | 25 | 12.5 | 12.5 |
| 42 | 0.78 | 0.78 | >100 | 25 | 6.25 | 50 | 3.12 |
| 43 | 0.39 | 0.2 | 50 | 6.25 | 6.25 | 6.25 | 3.12 |
| 45 | 0.78 | 0.39 | 100 | 100 | 25 | 25 | 6.25 |
| 46 | 0.78 | 0.39 | >100 | 50 | 1.25 | 12.5 | 6.25 |
| 54 | 0.05 | 0.05 | 6.25 | 25 | 6.25 | 1.56 | 1.56 |
| 57 | 0.0015 | 0.1 | >100 | >100 | 50 | 12.5 | 25 |
| 60 | 0.78 | 0.78 | 50 | 12.5 | >100 | 100 | 100 |
| 61 | 1.56 | 1.56 | 50 | 25 | >100 | 50 | 25 |
| 67 | 0.39 | 0.78 | 3.12 | 6.25 | 6.25 | 12.5 | 0.78 |
| 68 | 0.78 | 0.78 | 25 | >100 | >100 | 25 | 3.12 |
| 69 | 0.1 | 0.1 | 12.5 | 12.5 | >100 | 12.5 | 1.56 |
| 70 | 0.025 | 0.05 | 6.25 | 25 | >100 | 12.5 | 1.56 |
| 71 | 0.2 | 0.2 | 6.25 | 12.5 | 3.12 | 12.5 | 3.12 |
| 72 | 0.78 | 25 | 12.5 | 25 | 6.25 | 12.5 | 3.12 |
| 73 | 0.78 | 25 | 12.5 | 25 | 6.25 | 12.5 | 3.12 |
| 74 | 0.78 | 0.39 | 12.5 | 25 | 3.12 | 25 | 3.12 |
| 75 | 1.56 | 1.56 | 50 | 25 | 12.5 | 6.25 | 6.25 |

-continued

| Comp. No. | \multicolumn{7}{c}{Kinds of the test microorganisms} |
|---|---|---|---|---|---|---|---|
|  | 1 | 2 | 3 | 4 | 5 | 6 | 7 |
| 76 | 0.39 | 0.39 | 25 | 25 | 12.5 | 12.5 | 3.12 |
| 79 | 0.39 | 0.39 | 25 | 25 | 12.5 | 12.5 | 3.12 |
| 80 | 0.39 | 0.78 | 25 | 25 | >100 | 25 | 3.12 |
| 81 | 0.39 | 0.39 | 50 | 6.25 | 25 | 25 | 1.56 |
| 82 | 0.39 | 0.39 | 25 | 25 | >100 | 25 | 3.12 |
| 87 | 100 | 0.78 | 25 | 25 | 100 | 50 | 3.12 |
| 88 | 0.39 | 0.39 | >100 | 25 | 12.5 | 12.5 | 3.12 |
| 89 | 0.025 | 0.05 | 6.25 | 6.25 | 25 | 6.25 | 1.56 |
| 93 | 0.2 | 0.2 | 6.25 | 25 | >100 | 12.5 | 3.12 |
| 94 | 0.2 | 0.2 | 6.25 | 6.25 | 6.25 | 6.25 | 3.12 |
| 95 | 0.1 | 0.1 | 12.5 | 6.25 | >100 | 6.25 | 1.56 |
| 99 | 0.78 | 0.78 | 6.25 | 12.5 | 25 | 6.25 | 3.12 |
| 100 | 100 | 0.78 | 25 | 25 | >100 | 100 | 3.12 |
| 102 | 0.78 | 0.39 | 12.5 | 50 | 25 | 12.5 | 6.25 |
| 104 | 1.56 | 0.78 | 50 | 100 | 100 | 25 | 25 |
| 108 | 1.56 | 0.78 | >100 | 50 | 25 | 25 | 1.25 |
| 118 | 0.39 | 0.39 | 12.5 | 3.12 | 12.5 | 6.25 | 1.56 |
| 119 | 0.39 | 0.39 | >100 | 50 | 25 | 25 | 12.5 |
| 125 | 6.25 | 1.56 | 25 | >100 | 100 | 12.5 | >100 |
| 126 | 0.39 | 0.39 | 6.25 | 25 | 3.12 | 12.5 | 3.12 |
| C.R(*) | 3.12 | 1.56 | 100 | 50 | >100 | >100 | 25 |

Remarks:
(*)Control reference compound (VII)

TEST EXAMPLE 2

The effect of controlling the rice blast to be developed when applied to stems and leaves of plants is investigated by the following testing method, together with the obtained results tabulated in the below-shown table, whereby the compounds tested are indicated by the compound number as given in the Example 3:

I. Testing method
1. Pathogen: *Pyricularia oryzae*
2. Plant to be tested: Rice, species of Asahi No. 4, planted in a 9-cm pot with 10 seedlings of about 32-day old.
3. Inoculation: Through natural infection from leaves affected by rice blast.
4. Treatment with antimicrobial agents: A test compound is compounded in accordance with the procedure of Example 7, diluted at the fixed concentration, added with 0.2% of spreader (Dyne, trademark of Takeda Chemical Ind.), and applied 2 days after initiation of inoculation.
5. Partition: 2 pots per one section
6. Examination: Examination is carried out in accordance with "Criteria for the Ratio of Leaf-Blast Affected Surface Area" (Pages 4–7) in "Criteria for Surveying the Incidence of Diseases and Pests" published by Japanese Association of Plant Protection (2nd February, 1974), 7 days after inoculation.

II. Test results

| Comp. No. | Concn. ppm | Affected surface area ratio, % | Comp. No. | Concn. ppm | Affected surface area ratio, % |
|---|---|---|---|---|---|
| 1 | 500 | 2 | 15 | 500 | 0 |
| 2 | 500 | 0 | 16 | 500 | 0 |
| 3 | 500 | 0 | 17 | 500 | 0 |
| 4 | 500 | 2 | 18 | 500 | 0 |
| 5 | 500 | 0 | 19 | 500 | 2 |
| 6 | 500 | 0 | 20 | 500 | 0 |
| 7 | 500 | 0 | 21 | 500 | 0 |
| 8 | 500 | 1 | 22 | 500 | 1 |
| 9 | 500 | 0 | 23 | 500 | 3 |
| 10 | 500 | 1 | 24 | 500 | 3 |
| 11 | 500 | 2 | 25 | 500 | 2 |
| 12 | 500 | 0 | 26 | 500 | 0 |
| 13 | 500 | 1 | 27 | 500 | 0 |
| 14 | 500 | 2 | 28 | 500 | 0 |
| 29 | 500 | 0 | 60 | 500 | 0 |
| 30 | 500 | 1 | 61 | 500 | 2 |
| 31 | 500 | 1 | 64 | 500 | 1 |
| 33 | 500 | 1 | 67 | 500 | 0 |
| 34 | 500 | 3 | 68 | 500 | 0 |
| 35 | 500 | 0 | 69 | 500 | 0 |
| 36 | 500 | 2 | 70 | 500 | 0 |
| 37 | 500 | 0 | 71 | 500 | 0 |
| 38 | 500 | 0 | 72 | 500 | 0 |
| 39 | 500 | 0 | 73 | 500 | 1 |
| 40 | 500 | 0 | 74 | 500 | 0 |
| 41 | 500 | 0 | 75 | 500 | 0 |
| 42 | 500 | 3 | 76 | 500 | 0 |
| 43 | 500 | 1 | 77 | 500 | 0 |
| 45 | 500 | 0 | 78 | 500 | 0 |
| 46 | 500 | 0 | 79 | 500 | 3 |
| 48 | 500 | 0 | 80 | 500 | 0 |
| 49 | 500 | 0 | 81 | 500 | 1 |
| 50 | 500 | 1 | 82 | 500 | 0 |
| 51 | 500 | 3 | 83 | 500 | 2 |
| 52 | 500 | 3 | 88 | 500 | 1 |
| 53 | 500 | 0 | 89 | 500 | 0 |
| 54 | 500 | 0 | 90 | 500 | 2 |
| 55 | 500 | 0 | 91 | 500 | 0 |
| 56 | 500 | 0 | 94 | 500 | 0 |
| 57 | 500 | 0 | 95 | 500 | 0 |
| 96 | 500 | 1 | 120 | 500 | 0 |
| 99 | 500 | 0 | 121 | 500 | 0 |
| 101 | 500 | 0 | 122 | 500 | 0 |
| 102 | 500 | 1 | 123 | 500 | 0 |
| 103 | 500 | 0 | 125 | 500 | 0 |
| 104 | 500 | 0 | 126 | 500 | 0 |
| 105 | 500 | 2 | CR-1(*) | 20 | 5 |
| 107 | 500 | 0 | CR-2(**) | 500 | 8 |
| 108 | 500 | 1 | N-t(***) | — | 30 |
| 118 | 500 | 0 |  |  |  |
| 119 | 500 | 0 |  |  |  |

Remarks:
(*)Blasticidin S (Bla-S, trademark) employed as control reference.
(**)EDDP (Hinosan, trademark) employed as control reference.
(***)Non-treated.

TEST EXAMPLE 3

The effect of controlling the rice blast to be developed when applied on the water surfaces is investigated by the following testing method, along with the obtained results tabulated in the table given below, whereby the compounds tested are indicated by the compound number as given in Example 3.

I. Testing method

1. Pathogen: The same as described in Test Example 2.
2. Plant to be tested: The same as described in Test Example 2, except that the rice plant is grown in 1/10000 a Wagner pot.
3. Inoculation: The same as described in Test Example 2.
4. Treatment with antimicrobial agents: The test compound is compounded in accordance with the procedure of Example 7, and applied in the irrigated water, either directly at the predetermined concentration or after being diluted at such concentration. Inoculation is initiated 2 days after the application.
5. Partition: The same as described in Test Example 2
6. Examination: The same as described in Test Example 2.

II. Test results

| Comp. No. | Applied amount g/10a | Affected surface area ratio, % | Comp. No. | Applied amount g/10a | Affected surface area ratio, |
|---|---|---|---|---|---|
| 2 | 300 | 1 | 40 | 300 | 0 |
| 3 | 300 | 2 | 41 | 300 | 1 |
| 5 | 300 | 6 | 47 | 300 | 18 |
| 9 | 300 | 4 | 48 | 300 | 18 |
| 13 | 300 | 8 | 50 | 300 | 16 |
| 18 | 300 | 7 | 54 | 300 | 8 |
| 19 | 300 | 3 | 74 | 300 | 16 |
| 20 | 300 | 13 | 103 | 300 | 0 |
| 22 | 300 | 18 | 104 | 300 | 18 |
| 24 | 300 | 0 | 108 | 300 | 9 |
| 29 | 300 | 18 | CR-1(*) | 680 | 25 |
| 31 | 300 | 18 | CR-2(**) | 480 | 18 |
| | | | CR-3(***) | 300 | 48 |
| | | | N-t(****) | — | 80 |

Remarks:
(*)IBP (Kitazin P) employed as control refeference.
(**)Isoprothiolane employed as control reference.
(***)The compound (VII) in Test Example 1.
(****)Non-treated control.

TEST EXAMPLE 4

The effect of controlling Helminthosporium leaf spot of rice to be developed when applied to stems and leaves of plants is investigated by the following testing method, along with the obtained results tabulated in the table given below, whereby the compounds tested are indicated by the compound number as given in Example 3:

I. Testing method

1. Pathogen: *Helminthosporium oryzae*
2. Plant to be tested: The same as described in Test Example 2.
3. Inoculation: A suspension of fungal spores (spore concentration of 1 to $2\times10^5$/ml) formed by growing the cultures on a potato-sucrose-agar medium at 28° C. for 10 days is spray-inoculated, and the inoculated plants are kept for 2 days in an atmosphere at 28° C. and at 100% RH (relative humidity), then allowed to stand in a green house.
4. Treatment with antimicrobial agents: In the same manner as described in Test Example 2, except that inoculation is effected after application and air-drying.
5. Partition: The same as described in Test Example 2
6. Examination: 7 days after inoculation, examination is carried out in accordance with the modified method of "Criteria for Judgement of the Incidence Degree of Leaf Rust, Dwarf Leaf Rust and Black Rust of Wheat" (page 27) in "Criteria for Surveying the Incidence of Diseases and Pests" published by Japanese Association of Plant Protection (15th February, 1974).

II. Test results

| Comp. No. | Concn. ppm | Incidence degree of disease, % | Comp. No. | Concn. ppm | Incidence degree of disease, % |
|---|---|---|---|---|---|
| 1 | 500 | 1 | 20 | 500 | 1 |
| 2 | 500 | 1 | 21 | 500 | 1 |
| 3 | 500 | 1 | 23 | 500 | 1 |
| 4 | 500 | 1 | 24 | 500 | 1 |
| 5 | 500 | 2 | 25 | 500 | 1 |
| 6 | 500 | 1 | 26 | 500 | 1 |
| 8 | 500 | 1 | 27 | 500 | 1 |
| 9 | 500 | 1 | 28 | 500 | 1 |
| 10 | 500 | 1 | 29 | 500 | 1 |
| 11 | 500 | 1 | 30 | 500 | 1 |
| 12 | 500 | 1 | 31 | 500 | 1 |
| 13 | 500 | 1 | 32 | 500 | 1 |
| 14 | 500 | 1 | 33 | 500 | 1 |
| 15 | 500 | 1 | 34 | 500 | 1 |
| 16 | 500 | 1 | 35 | 500 | 1 |
| 17 | 500 | 1 | 37 | 500 | 1 |
| 18 | 500 | 1 | 38 | 500 | 1 |
| 19 | 500 | 1 | 39 | 500 | 1 |
| 40 | 500 | 1 | 69 | 500 | 1 |
| 41 | 500 | 1 | 70 | 500 | 1 |
| 42 | 500 | 1 | 71 | 500 | 1 |
| 43 | 500 | 1 | 72 | 500 | 1 |
| 44 | 500 | 1 | 73 | 500 | 1 |
| 45 | 500 | 1 | 75 | 500 | 1 |
| 46 | 500 | 1 | 76 | 500 | 1 |
| 47 | 500 | 1 | 77 | 500 | 1 |
| 48 | 500 | 5 | 79 | 500 | 1 |
| 49 | 500 | 1 | 80 | 500 | 1 |
| 50 | 500 | 5 | 81 | 500 | 1 |
| 51 | 500 | 1 | 83 | 500 | 1 |
| 52 | 500 | 1 | 87 | 500 | 1 |
| 53 | 500 | 1 | 89 | 500 | 1 |
| 54 | 500 | 1 | 90 | 500 | 1 |
| 55 | 500 | 1 | 93 | 500 | 1 |
| 58 | 500 | 2 | 94 | 500 | 1 |
| 59 | 500 | 5 | 95 | 500 | 2 |
| 60 | 500 | 1 | 96 | 500 | 1 |
| 61 | 500 | 1 | 99 | 500 | 1 |
| 62 | 500 | 5 | 100 | 500 | 2 |
| 63 | 500 | 1 | 101 | 500 | 1 |
| 64 | 500 | 1 | 102 | 500 | 1 |
| 66 | 500 | 5 | 103 | 500 | 1 |
| 67 | 500 | 1 | 104 | 500 | 1 |
| 68 | 500 | 1 | 105 | 500 | 1 |
| 106 | 500 | 1 | 115 | 500 | 5 |
| 107 | 500 | 1 | 117 | 500 | 1 |
| 108 | 500 | 5 | CR-1(*) | 500 | 25 |
| 111 | 500 | 1 | N-t(**) | — | 50 |
| 112 | 500 | 5 | | | |

Remarks:
(*)EDDP (Hinosan) employed as control reference
(**)Non-treated control.

TEST EXAMPLE 5

The effect of controlling Helminthosporium leaf spot of rice to be developed when applied on water surfaces is investigated by the following testing method, together with the obtained results tabulated in the table given below, whereby the compounds tested are indicated by the compound number as given in Example 3:

I. Testing method
1. Pathogen: The same as described in Test Example 4
2. Plant to be tested: The same as described in Test Example 2.
3. Inoculation: In the same manner as described in Test Example 4.
4. Treatment with antimicrobial agents: In the same manner as described in Test Example 4.
5. Partition: The same as described in Test Example 2
6. Examination: In the same manner as described in Test Example 4.

II. Test results

| Comp. No. | Applied amount g/10a | Incidence degree of disease, % | Comp. No. | Applied amount g/10a | Incidence degree of disease, % |
|---|---|---|---|---|---|
| 2 | 300 | 0 | 39 | 300 | 5 |
| 3 | 300 | 2 | 40 | 300 | 1 |
| 9 | 300 | 1 | 41 | 300 | 2 |
| 13 | 300 | 2 | 42 | 300 | 3 |
| 16 | 300 | 1 | 43 | 300 | 3 |
| 17 | 300 | 4 | 54 | 300 | 5 |
| 18 | 300 | 5 | 74 | 300 | 2 |
| 19 | 300 | 1 | 75 | 300 | 7 |
| 20 | 300 | 1 | 103 | 300 | 1 |
| 26 | 300 | 8 | CR-1(*) | 680 | 68 |
| 31 | 300 | 2 | CR-2(**) | 500 | 68 |
| 38 | 300 | 1 | CR-3(***) | 300 | 20 |
|  |  |  | N-t(****) | 300 | 80 |

Remarks:
(*)IBP (Kitazin P) employed as control reference.
(**)EDDP (Hinosan) employed as control reference.
(***)The compound (VII) in Test Example 1.
(****)Non-treated control.

TEST EXAMPLE 6

The effect of controlling the rice sheath blight is investigated by the following testing method, together with the obtained results tabulated in the table given below, whereby the compounds tested are indicated by the compound number as given in Example 3.

I. Testing method
1. Pathogen: *Pellicularia sasakii* (*Rhizoctonia solani sasakii* type)
2. Plant to be test: Rice plant; species of Kinmaze, planted in 9 cm pots with 3 seedlings of 80 to 90-day old.
3. Inoculation: The peripheral portion of a mycelial colony grown on a potato-sucrose-agar medium at 28° C. for 2 days is stamped out by a cork borer of 10 mm in diameter, and inserted into a stem portion of a rice plant near the ground, followed by maintaining at a temperature of 25° to 35° C. and a relative humidity of 70 to 100% after the inoculation and until the examination is effected.
4. Treatment with antimicrobial agents: In the same manner as described in Test Example 2, except that inoculation is effected after application and air-drying.
5. Partition: 2 pots per one section
6. Examination: 10 days after inoculation, the height from the base stem portion to the upper end of diseased spot is measured to calculate a diseased spot expansion ratio in relation to that found in the non-treated section II. Test results

| Comp. No. | Concn. ppm | Diseased spot expansion rate % | Comp. No. | Concn. ppm | Diseased spot expansion rate % |
|---|---|---|---|---|---|
| 2 | 500 | 0 | 19 | 500 | 0 |
| 3 | 500 | 0 | 20 | 500 | 4 |
| 13 | 500 | 1 | 22 | 500 | 0 |
| 15 | 500 | 0 | 33 | 500 | 0 |
| 17 | 500 | 0 | 37 | 500 | 3 |
| 39 | 500 | 0 | 82 | 500 | 4 |
| 40 | 500 | 0 | 89 | 500 | 0 |
| 43 | 500 | 0 | 94 | 500 | 5 |
| 44 | 500 | 4 | 95 | 500 | 10 |
| 46 | 500 | 0 | 104 | 500 | 0 |
| 49 | 500 | 0 | CR-1(*) | 30 | 0 |
| 54 | 500 | 4 | CR-2(**) | 250 | 52 |
| 81 | 500 | 0 | N-t(***) | — | 100 |

Remarks:
(*)Validamycin A (Validacin) employed as control reference.
(**)The compound (VII) in Test Example 1.
(***)Non-treated control.

What we claim is:

1. A pyrimidine derivative of the formula:

$$Ar-\underset{R^1}{C}=N-\underset{R^2}{N}-\underset{\substack{N \\ \| \\ N}}{\overset{R^3}{\underset{R^5}{\bigg\langle}}}-R^4$$

wherein Ar is phenyl, naphthyl, phenyl having 1 to 5 substituents or naphthyl having 1 to 7 substituents, said substituents being selected from the group of lower alkyl, lower alkoxy, lower alkylthio, lower alkylsulfinyl, lower alkylsulfonyl, halogen, nitro, trifluoromethyl and di-lower alkylamino, $R^1$ is lower alkyl, lower cycloalkyl, trifluoromethyl, lower alkoxycarbonyl, phenyl, benzyl, or phenyl having 1 to 5 halogen substituents, $R^2$ is hydrogen or lower alkyl, $R^3$, $R^4$ and $R^5$ are hydrogen, lower alkyl, lower alkenyl or lower alkoxy, or $R^3$ and $R^4$ or $R^4$ and $R^5$ combine with each other to represent trimethylene, tetramethylene or butadienylene, or a salt thereof.

2. A pyrimidine derivative as claimed in claim 1, wherein Ar is phenyl or phenyl substituted by 1 to 5 substituents from the group of lower alkyl, lower alkoxy, lower alkylthio, halogen and trifluoromethyl, $R^1$ is lower alkyl or lower cycloalkyl, $R^3$, $R^4$ and $R^5$ are hydrogen, lower alkyl or lower alkenyl, or $R^3$ and $R^4$ or $R^4$ and $R^5$ combine with each other to represent trimethylene, tetramethylene or butadienylene.

3. A pyrimidine derivative as claimed in claim 1, wherein Ar is phenyl having 1 to 5 substituents from the group of lower alkyl and halogen, $R^1$ is lower alkyl, $R^2$ is hydrogen, $R^3$, $R^4$ and $R^5$ are lower alkyl or lower alkenyl, or $R^4$ and $R^5$ combine with each other to represent butadienylene.

4. A pyrimidine derivative as claimed in claim 1, wherein Ar is phenyl having 1 to 5 lower alkyl substituents, $R^1$ is lower alkyl, $R^2$ is hydrogen, $R^3$ and $R^5$ are lower alkyl, and $R^4$ is hydrogen.

5. A pyrimidine derivative as claimed in claim 1, which is 4,6-dimethyl-2-[1-(2-methylphenyl)ethylidenehydrazino]-pyrimidine.

6. A pyrimidine derivative as claimed in claim 1, which is 4,6-dimethyl-2-[1-(2,5-dimethylphenyl)ethylidenehydrazino]-pyrimidine.

7. A pyrimidine derivative as claimed in claim 1, which is 4,6-dimethyl-2-[1-(2,4,6-trimethylphenyl)-ethylidenehydrazino]pyrimidine.

8. An antimicrobial agent for agricultural uses which contains as an active ingredient a pyrimidine derivative of the formula:

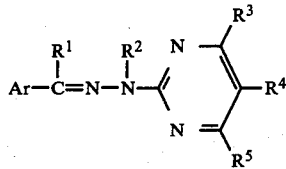

wherein Ar is phenyl, naphthyl, phenyl having 1 to 5 substituents or naphthyl having 1 to 5 substituents said substituents being selected from the group of lower alkyl, lower alkoxy, lower alkylthio, lower alkylsulfinyl, lower alkylsulfonyl, halogen, nitro, trifluoromethyl and di-lower alkylamino, $R^1$ is lower alkyl, lower cycloalkyl, trifluoromethyl, lower alkoxycarbonyl, phenyl, benzyl or phenyl having 1 to 5 halogen substituents, $R^2$ is hydrogen or lower alkyl, $R^3$, $R^4$ and $R^5$ are hydrogen, lower alkyl, lower alkenyl or lower alkoxy, or $R^3$ and $R^4$ or $R^4$ and $R^5$ combine with each other to represent trimethylene, tetramethylene or butadienylene, or a salt thereof, together with a suitable carrier or carriers.

* * * * *